Figure 1:
Figure 2:
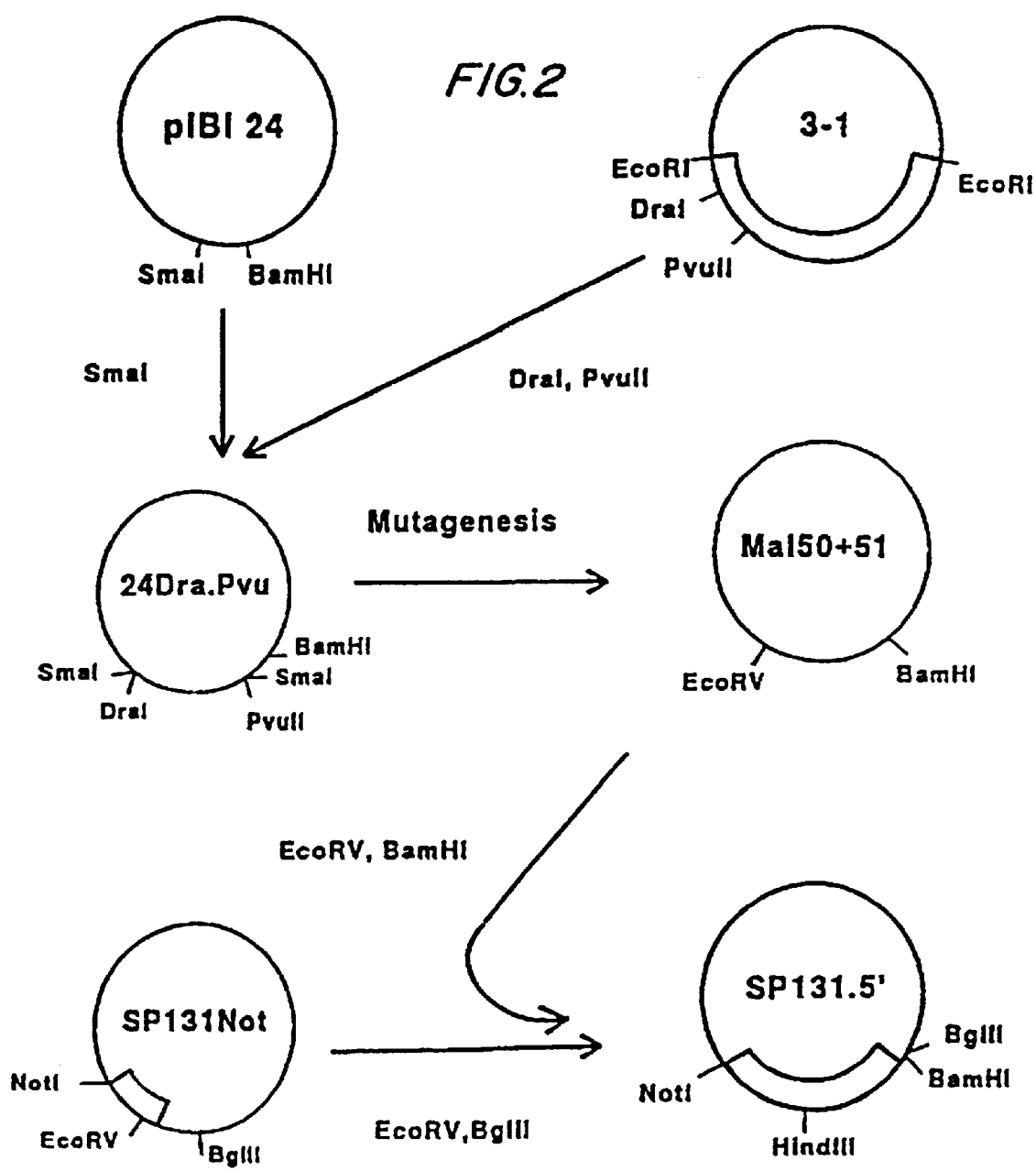
Figure 3:
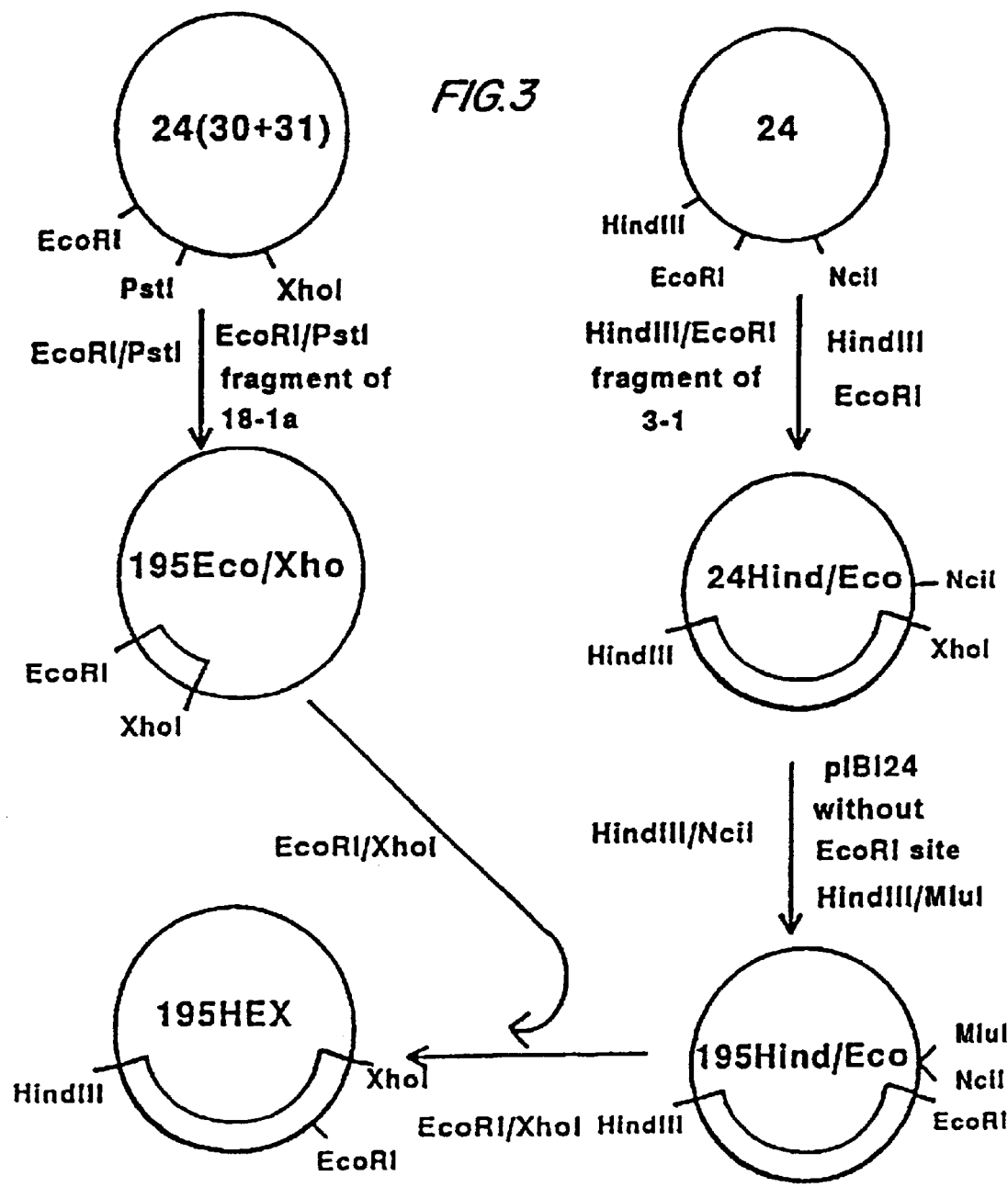

US006214353B1

(12) United States Patent
Paoletti et al.

(10) Patent No.: US 6,214,353 B1
(45) Date of Patent: Apr. 10, 2001

(54) MALARIA RECOMBINANT POXVIRUS VACCINE

(75) Inventors: Enzo Paoletti, Delmar, NY (US); Charles de Taisne, Lyons (FR); Sandra Chang, Honolulu, HI (US); George Hui, Honolulu, HI (US); Wasim A. Siddigui, Honolulu, HI (US)

(73) Assignees: Pasteur Merieux Serums et Vaccins, Lyons (FR); The University of Hawaii, Honolulu, HI (US)

( * ) Notice: Subject to any disclaimer, the term of this patent is extended or adjusted under 35 U.S.C. 154(b) by 0 days.

(21) Appl. No.: 09/083,366

(22) Filed: May 21, 1998

Related U.S. Application Data

(62) Division of application No. 08/178,476, filed on Jan. 7, 1994, now Pat. No. 5,756,101, which is a continuation of application No. 07/724,109, filed on Jul. 1, 1991, now abandoned.

(51) Int. Cl.[7] ...................... A61K 39/285; A61K 39/295; A61K 39/275; A61K 39/015; C12N 7/01

(52) U.S. Cl. .................................... 424/199.1; 435/235.1; 435/320.1; 435/69.3; 424/272.1; 424/232.1; 424/268.1

(58) Field of Search .............................. 435/235.1, 320.1, 435/69.3, 199.1; 424/272.1, 232.1

(56) References Cited

U.S. PATENT DOCUMENTS

| | | | |
|---|---|---|---|
| 4,603,112 | 7/1986 | Paoletti . | |
| 5,110,587 | 5/1992 | Paoletti . | |
| 5,597,708 * | 2/1985 | Holder et al. | 435/69.3 |

FOREIGN PATENT DOCUMENTS

| | | | |
|---|---|---|---|
| 0 198 328 | 10/1986 | (EP) . | |
| 89/034299 * | 4/1989 | (WO) | C12N/15/00 |

OTHER PUBLICATIONS

Cao, Y et a;., Journal of Cellular Biochemistry, sup 15F, pp. 220–abstract CF107 (1991).

Chang, S.P., Hui, G.S.N. Kato, A., Siddiqui, W.A., Proc. Natl.Acad. Sci. USA 86, 6343–6347 (1989).

Chang, S.P., Kramer, K.J., Yamaga, K.M., Kato, A., Case, S.E., Siddiqwui, W.A., Exp. Para. 67, 1–11 (1988).

Cheung, A., Leban, J., Shaw, A.R., Merkli, B., Stocker, J., Chizzolini, C., Sander, C., Perrin, L.H., Proc. Natl. Acad. Sci. USA. 83, 8328–8332 (1986).

Clewell, D.B., J. Bacteriol. 110, 667–676 (1972).

Clewell, D.B. and Helinski, D.R., Proc. Natl. Acad. Sci. USA 62, 1159–1166 (1969).

Database Derwent Biotechnology Abstracts, DBA Accession no. 91–12843, Fodor, Acta Biotechnol, vol. 11, pp. 219–225, abstract only (1991).

Database Derwent Biotechnology Abstracts, DBA Accession no. 91–11080, patent WO 9109124, abstract only (Jun. 27, 1991).

Database Derwent Biotechnology Abstracts, DBA Accession no. 91–08572, Redmond Et asl., Genet. Eng. Biotechnol., vol 11 pp. 14–21, abstract onbly (1991).

Database Derwent Biotechnology Abstracts, DBA Accession no. 91–04979, patent WO 9100904, abstract only (Ja. 1, 1991).

Database Derwent Biotechnology Abstracts, DBA Accession no. 90–02591, patent EP 345242, abstract only (Dec. 6, 1989).

Database Derwent Biotechnology Abstracts, DBAS Accession no. 89–08168, patent EP 307149, abstract only (Mar. 15, 1989).

Database Derwent Biotechnology Abstracts, DBA Accession no. 89–03297, patent WO 880817, abstract only (Dec. 15, 1988).

Database Derwent Biotechnology Abstracts, DBAS Accession no. 87–13518, patent AU 876820, abstract only (Aug. 13, 1987).

Database Derwent Biotechnology Abstracts, DBA Accession no. 87–02405, Levine et al., abstract only (1985).

Dreyfuss, G., Adam, S.A., Choi, Y.D., Mol. Cell. Bio. 4, 415–423 (1984).

Ferguson, M., TIBTECH, vol. 9 pp. 7–11 (1991).

Guo, P., Goebel, S., Davis, S., Perkus, M.E., Languet, B., Desmettre, P., Allen, G., Paoletti, E., J. Virol. 63, 4189–4198 (1989).

Hall, R., Hyde, J.E., Goman, M., Simmons, D.L., Hope, I.A., Mackay, J., Richle, R., Nature 311, 279–392 (1984).

Herrera, S., Herrera, M.A., Perlaza, B.L., Burki Y., Caper, P., Dobeli, H., Rotmann, D., Certa, U., Proc. Natl. Acad. Sci. USA 87, 4017–4021 (1990).

Holder, A.A., Prog. Allergy 41, 72–97 (1988a).

Holder, A.A., Freeman, R.R. Nicholls, S.C., Parasit. Immunol. 10, 607–617 (1988b).

Hui, G.S.N., Siddiqui, W.A., Exp. Pata. 64, 519–522 (1987).

Iacono–Connors, L.C. et al., Infection and Immunity, vol. 58, pp. 366–372 (1990).

Knapp, B., Shaw, A., Hundt, E., Ebders, B., Kupper, H.A., Behring Inst. Mitt. 82, 349–359 (1988).

Kunkle, T.A., Roberts, J.D., Zakour, R.A., Methods Enzymol. 154, 367–382 (1987).

Langford et al., (Vaccines 1988) 89–94 1988.

Lew, A.M. et al., 1985 Proc. National Acad. Sci. USA, Vol. 86, pp. 3768–3772.

(List continued on next page.)

*Primary Examiner*—Mary E. Mosher
(74) *Attorney, Agent, or Firm*—Frommer Lawrence & Haug LLP; William S. Frommer; Thomas J. Kowalski

(57) ABSTRACT

What is described is a recombinant poxvirus, such as vaccinia virus, containing foreign DNA from Plasmodium Merozoite Surface Antigen 1. What is also described is a vaccine containing the recombinant poxvirus for inducing an immunological response in a host animal inoculated with the vaccine.

8 Claims, 4 Drawing Sheets

OTHER PUBLICATIONS

Lyon, J.A., Haynes, J.D., Diggs, C.L., Chulay, J.D., Haidaris, C.G., Pratt–Rossiter, J., J. Immunol. 138, 895–901 (1987).

Maniatis, T., Fritsch, E.F., Sambrock, J., *In* Molecular Cloning: A Laboratory Manual (Cold Spring Harbor Laboratory, Clod Spring Harbor, NY) (1982).

Morgan et al., J. Med. Virol 25, 189–195, (1988).

Murphy, V.F. et al., 1990 Parasitology, Vol. 100, pp. 177–183.

Panicali, D., Paoletti, E., Proc. Natl. Acad. Sci. USA 79, 4927–(1982).

Patarroyo, M.E., Amador, R., Clavijo, P., Moreno, A., Guzman, F., Romero, P., Tascon, R., Franco, A., Murillo, L.A. Ponton, G., Trujillo, G., Nature 322, 158–161 (1988).

Patarroyo, M.E., Romero, P., Torres, M.L., Clavijo, P., Moreno, A., Martinez, A., Rodriguez, R., Guzman, F., Cabezas, E., Nature 328, 629–632 (1987).

Perkus, M.E., Goebel, S.J., Davis, S.W., Johnson, G.P., Limbach, K., Norton, E.K., Paoletti, E., Virology 170, 276–286 (1990).

Perkus, M., Goebel, S., Davis, S., Johnson, G., Norton, E., and Paoletti, E., Virol. 180, 406–410 (1991).

Perrin, L.H., Merkli, B., Loche, M., Chizzolini, C., Smart, J., and Richle, R., J. Exp. Med. 160, 441–451 (1984).

Peterson, M.G., Coppel, R.L., Moloney, M.B., Kemp, D.J., Mol. Cell. Biol. 8, 2664–2667 (1988).

Petrovskis, E.A. et al., Journal of Cellular Biocheminstry, sup. 12B, pp. 22, abstract F 209.

Piccini, A., Perkus, M.E. and Paoletti, E., *In* Methods in Enzymology, Vol. 153, eds. Wu, R., and Grossman, L., (Academic Press) pp. 545–563 (1987).

Pye et al., Infec. Immum. 59, 2403–2411, (1991).

Sambrook, J., Fritsch, E.F., and Maniatis, T., *In* Molecular Cloning: A laboratiry manual, $2^{nd}$ edition, (Cold Spring Harbor Press,NY) (1989).

Sanger, F., Nicklen, S., Coulson, A.R., Proc. Natl. Acad. Sci. USA 74 5463–5467 (1977).

Satchidanandam et al., Molec. Biochem. Parasitol. 48–49, 89–100, (1991).

Schmaljohn, C.S. et al., Journal of Virology, Vol. 64 pp. 3162–3170 (1990).

Siddiqui, W.A., Tam, L.Q., Kan S.C., Kramer, K.J., Case, S.E., Palmer, K.L., Yamaga, K.M., Hui, G.S., Infect. Immun. 52, 314–318 (1986).

Siddiqui, W.A., Tam, L.Q., Kramer, K.J., Jui, G.S.N., Case, S.E., Yamaga, K.M., Chang, S.P., Chan, E.B.T., Kan, S.C., Proc. Natl. Acad. Sic. USA 84, 3014–3018 (1987).

Tanabe, K., Mackay, N., Goman, M., Scaife, J.G., J. Mol. Biol. 195, 273–287 (1987).

Tartaglia et al., Virol. 217–232, (1992).

Taylor, J., Weinberg, R., Kawaoka, L., Webster, R.C., and Paoletti, E, Vaccine 6, 504–506 (1988a).

Taylor, J., Weinberg, R., Lamguet, B., Desmettre, P., and Paoletti, E., Vaccine 6, 497–503 1988b).

Taylor, J., Pincus, S., Trataglia, J., Richardson, C., Alkhatib, G., Briedis, D., Appel, M., Norton, E., and Paoletti,m E., Virol. 65, in press (1991).

Whang, Y., Silberkalang, M., Morgan, A., Munshi, S., Lenny, A.B., Ellis, R.W., Kieff, E., J. Virol. 61, 17696–1807 (1987).

Yuen, L., Moss, B., Proc. Natl. Acad. Sci. USA 84, 6417–6421 (1987).

Zuckerman, A., Vaccine, Vol. 5 pp. 165–167 (1987).

Miller, L.H. et al. Molecular and Biochemical Parasitology 59:1–14 1993.*

Lewis, A.O. Molecular and Biochemical Parasitology 36:271–282 Oct. 1989.*

Peterson, M.G., et al. Molecular and Biochemical PArasitology 27: 291–302. Jan. 1988.*

Kimura, E. et al. Gene 91: 57–62. Jul. 1990.*

Deleersnidjer, W. et al. Molecular and Biochemical Parasitolgy 43: 231–244. Dec. 1990.*

Jongwutiwes, S. et al. Am J Trop Med Hyg 44 (3): 299–305 (Abstract only cited). Mar. 1991.*

* cited by examiner

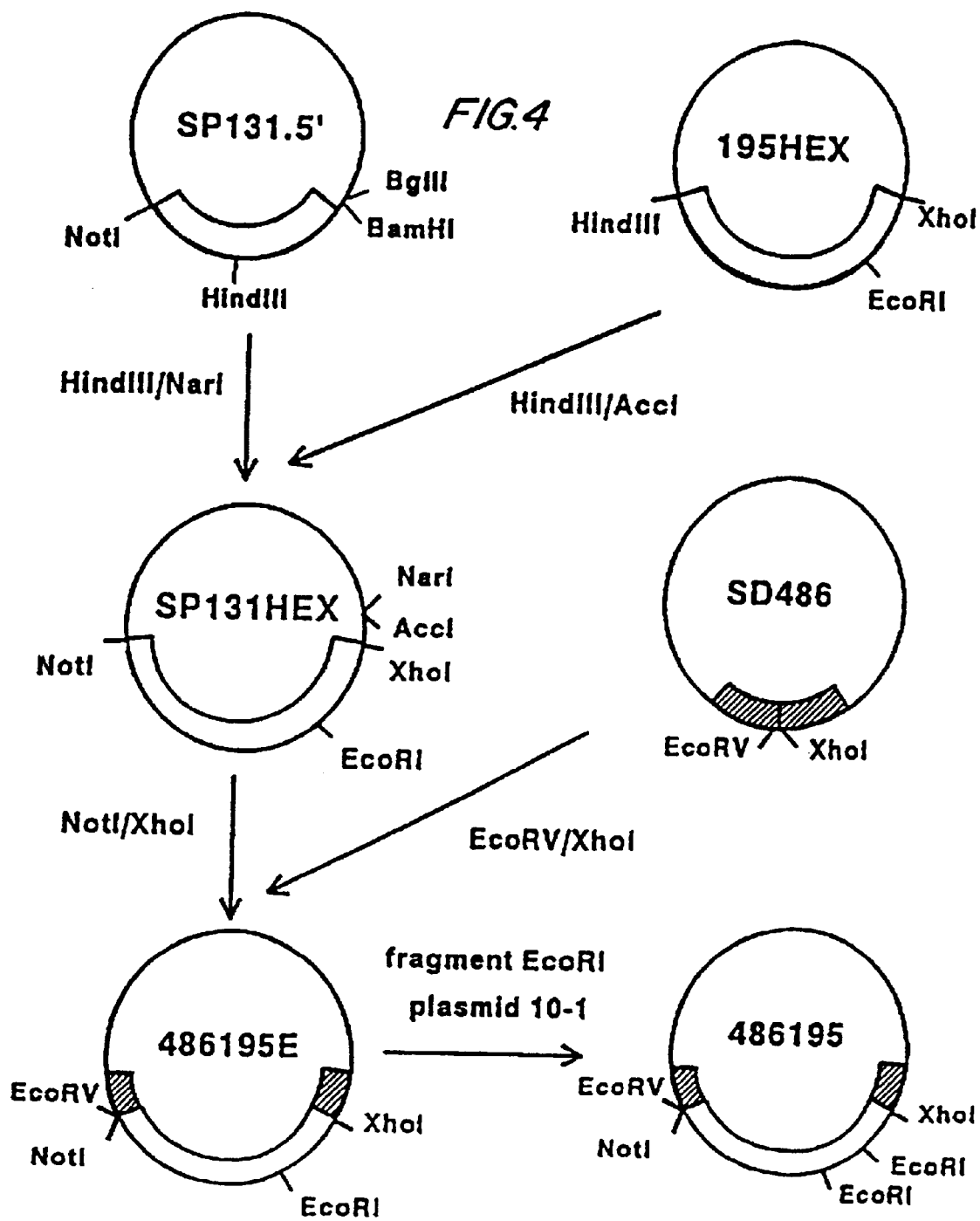

MALARIA RECOMBINANT POXVIRUS VACCINE

RELATED APPLICATIONS

This application is a divisional of U.S. application Ser. No. 08/178,476, filed Jan. 7, 1994, now U.S. Pat. No. 5,756,101, issued May 26, 1998, which is a continuation of U.S. application Ser. No. 07/724,109, filed Jul. 1, 1991, now abandoned.

FIELD OF THE INVENTION

The present invention relates to a modified poxvirus and to methods of making and using the same. More in particular, the invention relates to recombinant poxvirus, which virus expresses gene products of a Plasmodium gene, and to vaccines which provide protective immunity against Plasmodium infections.

Several publications are referenced in this application. Full citation to these references is found at the end of the specification preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell et al., 1969; Sambrook et al., 1989).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

The technology of generating vaccinia virus recombinants has recently been extended to other members of the poxvirus family which have a more restricted host range. The avipoxvirus, fowlpox, has been engineered as a recombinant virus expressing the rabies G gene (Taylor et al., 1988a,b). This recombinant virus is also described in PCT Publication No. WO089/03429. On inoculation of the recombinant into a number of non-avian species an immune response to rabies is elicited which in mice, cats and dogs is protective against a lethal rabies challenge.

Malaria today still remains one of the world's major health problems. It is estimated that 200–300 million malaria cases occur annually while 1–2 million people, mostly children, die of malaria each year. Malaria in humans is caused by one of four species of the genus Plasmodium— *P. falciparum, P. vivax, P. malariae,* and *P. ovale*. Clinically, *P. falciparum* is the most important human Plasmodium parasite because this species is responsible for most malaria fatalities.

A *Plasmodium falciparum* infection starts with the bite of an infected female Anophele mosquito. Its saliva contains sporozoites that migrate in the blood vessels to reach their first targets, the hepatocytes. After invasion, the sporozoites undergo a first multiplication stage lasting between five to seven days (exoerythrocytic phase or liver stage). Each hepatocyte can release 10,000 to 40,000 merozoites into the blood stream. Merozoites infect the second cellular target, the erythrocytes, where they multiply during a 48 to 72 hour cycle (erythrocytic stage). Each infected erythrocyte can release 16 merozoites able to infect new erythrocytes. The clinical symptoms of malaria appear during the blood stage infection. Infected erythrocytes can also produce gametocytes that mature and fuse in the mosquito midgut to form the zygotes. The zygotes evolve into ookinetes that develop into oocystes which, after infection of epithelial cells, produce sporozoites. The sporozoites migrate into the salivary glands from where they can initiate a new human infection.

The acquisition of protective immunity against malaria in naturally infected people is a slow process requiring multiple infections and is *Plasmodium falciparum* specific. The components that elicit immunity and the exact nature of this protective immune response are largely unknown but include activation of both specific and non-specific humoral and cellular mechanisms directed against a variety of sporozoite, liver stage and erythrocytic stage antigens.

MSA1 (Merozoite Surface Antigen 1), also referred to as PMMSA, p195 and PSA, is the best characterized biochemically and immunologically asexual erythrocytic antigen. It has been used alone and in combination with other blood stage antigens to vaccinate humans and monkeys against malaria.

MSA1 is a schizont surface glycoprotein which is proteolytically cleaved at the time of schizont rupture to generate the majority of the antigens detected on the extracellular surface of the merozoites (Lyon et al., 1987; Holder, 1988a). During merozoite invasion in vitro all but the C-terminal 19 kd of MSA1 are shed. The precise role of MSA1 is still unknown. Polymorphism has been reported in this protein among various *Plasmodium falciparum* isolates and constant, semi-constant and variable regions have been localized within the molecule. A more precise analysis determined that the polymorphism could be reduced to a dimorphism (Tanabe et al., 1987) even if three distinct versions of one of the variable regions have been identified (Peterson et al., 1988).

MSA1 is probably one of the strongest malarial vaccine candidates. This is supported by ten different reports of vaccine trials in which primates have been immunized with complete MSA1 or derived peptides and challenged with infected erythrocytes (Perrin et al., 1984; Hall et al., 1984; Cheung et al., 1986; Siddiqui et al., 1986; Siddiqui et al., 1987; Patarroyo et al., 1987; Patarroyo et al., 1988; Holder et al., 1988; Knapp et al., 1988; Herrera et al., 1990).

In the search for a malaria vaccine, the possibility of using a live recombinant vaccine has not been extensively studied. Indeed, the majority of the malaria vaccines are purified native antigens or synthetic peptides derived from them.

It can be appreciated that provision of a malaria recombinant poxvirus, and of vaccines which provide protective immunity against Plasmodium infections, would be a highly desirable advance over the current state of technology.

OBJECTS OF THE INVENTION

It is therefore an object of this invention to provide recombinant poxviruses, which viruses express gene products of Plasmodium, and to provide a method of making such recombinant poxviruses.

It is an additional object of this invention to provide for the cloning and expression of Plasmodium coding sequences, particularly the complete MSA1 gene and subfragments of the MSA1 gene, in a poxvirus vector, particularly vaccinia virus.

It is another object of this invention to provide a vaccine which is capable of eliciting malaria antibodies and protective immunity against Plasmodium infection.

These and other objects and advantages of the present invention will become more readily apparent after consideration of the following.

STATEMENT OF THE INVENTION

In one aspect, the present invention relates to a recombinant poxvirus containing therein a DNA sequence from Plasmodium in a nonessential region of the poxvirus genome. The poxvirus is advantageously a vaccinia virus or an avipox virus, such as fowlpox virus or canarypox virus.

According to the present invention, the recombinant poxvirus expresses gene products of the foreign Plasmodium gene. In particular, the foreign DNA codes for the complete MSA1 gene or subfragments of the MSA1 gene. Advantageously, the MSA1 gene is co-expressed with other foreign genes in the host by the recombinant poxvirus.

In another aspect, the present invention relates to a vaccine for inducing an immunological response in a host animal inoculated with the vaccine, said vaccine including a carrier and a recombinant poxvirus containing, in a nonessential region thereof, DNA from Plasmodium. Advantageously, the DNA codes for and expresses a MSA1 gene or subfragments of the MSA1 gene. The MSA1 gene advantageously is co-expressed with other foreign genes in the host. The poxvirus used in the vaccine according to the present invention is advantageously a vaccinia virus or an avipox virus, such as fowlpox virus or canarypox virus.

BRIEF DESCRIPTION OF THE DRAWINGS

A better understanding of the present invention will be had by referring to the accompanying drawings, in which:

FIG. 1 is a schematic representation of the MSA1 gene shown above the relative position of the four clones derived from an EcoRI genomic library;

FIG. 2 schematically shows a method for the construction of plasmid SP131.5';

FIG. 3 schematically shows a method for the construction of plasmid 195HEX; and FIG. 4 schematically shows a method for the construction of plasmid 486195.

DETAILED DESCRIPTION OF THE INVENTION

The invention is directed to recombinant poxviruses containing therein a DNA sequence from Plasmodium in a nonessential region of the poxvirus genome. The recombinant poxviruses express gene products of the foreign Plasmodium gene. For example, *P. falciparum* genes were expressed in live recombinant poxviruses. In particular, the complete MSA1 gene or subfragments of the MSA1 gene were isolated, characterized and inserted into vaccinia virus recombinants.

Enzymes and Plasmids. Restriction enzymes were obtained from GIBCO/BRL, Gaithersburg, Md.; New England Biolabs, Inc., Beverly, Mass.; and Boehringer-Mannheim, Indianapolis, Ind. T4 DNA ligase, Mung-bean nuclease, and DNA polymerase I Klenow fragment were obtained from New England Biolabs, Inc. Standard recombinant DNA techniques were used (Maniatis et al., 1982) with minor modifications for cloning, screening and plasmid purification. Nucleic acid sequences were confirmed using standard dideoxychain-termination reactions (Sanger et al., 1977) on alkaline-denatured double-stranded plasmid templates. pIBI24 and pIBI25 plasmids were obtained from International Biotechnologies, Inc., New Haven, Conn.

Cell Lines and Virus Strains. A thymidine kinase mutant of the Copenhagen vaccinia strain virus vP410 (Guo et al., 1989) as well as a vaccinia host range mutant (Perkus et al., 1991) were used to generate MSA1 recombinants. All vaccinia virus stocks were produced in either Vero (ATCC CCL81) or MRC5 (ATCC CCL71) or RK-13 (ATCC CCL37) cells in Eagles MEM medium supplemented with 5–10% newborn calf serum (ICN/Flow Laboratories, McLean, Va.).

Oliaonucleotide-directed Mutagenesis. The uracil-substituted single-stranded DNA template used for the mutagenesis reactions was isolated from CJ236 transformed cells. The mutations were achieved by using the protocol of Kunkel et al. (1987). The various oligonucleotides were synthesized using standard chemistries (Biosearch 8700, San Rafael, Calif.; Applied Biosystems 380B, Foster City, Calif.).

EXAMPLE 1

Reconstruction of the Complete MSA1 Gene and Modification for Vaccinia Expression Modifications of the 5' Extremity of the MSA1 Gene. Referring now to FIG. 1, the complete MSA1 gene of the Uganda Palo-Alto isolate was isolated in four fragments cloned into M13 and pUC derived vectors (Chang et al., 1988). The MSA1 open reading frame is 5181 nucleotides long and codes for a 1726 amino acid protein. (In all descriptions of manipulations of this gene, the adenine residue of the initiation codon will be used as nucleotide 1 and the first methionine residue as amino acid 1.)

The complete gene has been expressed under the control of the early/late H6 vaccinia promoter (Taylor et al., 1988a, b) by modifying the 5' first 21 nucleotides (position −21 to −1) to reconstitute the exact nucleotide sequence of the H6 promoter. Referring now to FIG. 2, this step was accomplished by cloning the DraI/PvuII 520 bp fragment from clone 3-1 into SmaI digested pIBI24; the resulting plasmid was called 24Dra/PvuII. By in vitro mutagenesis (Kunkel et al., 1987) using the oligonucleotide MAL51 (SEQ ID NO:1) the 5' extremity of the MSA1 gene was adapted for expression under the control of the vaccinia H6 promoter.

The PstI site is localized at position 5113 in the MSA1 gene.

MAL30 (SEQ ID NO:3) and MAL31 (SEQ ID NO:4) were annealed and cloned into a PstI/XhoI digested pIBI24 plasmid. The resulting plasmid was called 24 (30+31).

Reconstruction of the Complete MSA1 Gene. Referring now to FIG. 3, the 850 bp EcoRI/PstI fragment from clone 18-1a was ligated into EcoRI/PstI digested 24 (30+31) plasmid. The resulting plasmid was called 195Eco/Xho.

The 3208 bp HindIII/EcoRI fragment from clone 3-1 was ligated into HindIII/EcoRI digested pIBI24 plasmid. The resulting plasmid was called 24Hind/Eco.

The 3910 bp NciI/HindIII fragment from 24Hind/Eco was ligated into MluI/HindIII digested pIBI24 (EcoRI$^-$) plasmid. The resulting plasmid was called 195Hind/Eco.

The 820 bp EcoRI/XhoI fragment from 195Eco/Xho plasmid was ligated into EcoRI/XhoI digested 195Hind/Eco plasmid. The resulting plasmid was called 195HEX (FIG. 3).

Referring now to FIG. 4, the 4145 bp HindIII/AccI fragment from 195HEX was ligated into HindIII/NarI digested SP131.5' plasmid. The resulting plasmid was called SP131HEX.

The 4350 bp NotI/XhoI fragment from SP131HEX was ligated into the EcoRV/XhoI digested vaccinia donor plasmid SD486. The resulting plasmid was called 486195E.

The 957 bp EcoRI fragment from clone 10-1 was ligated into the EcoRI digested plasmid 486195E. The resulting vaccinia donor plasmid carrying the complete MSA1 (p195) gene was called 486195 (FIG. 4).

The 5210 bp NruI/XhoI fragment from 486195 was cloned into the NruI/XhoI digested mp598 plasmid (mp598 was derived from SD494 by insertion of the vaccinia H6 promoter (Perkus et al., 1990). The resulting plasmid was called AtiH6195.

```
MAL51: AAAGAATATGATCTTCATTACGATACAAACTTAACGGATATCCCTATAGTGAGTCGTA
                     GTA                        EcoRV
```

Simultaneously, a second mutagenesis was conducted to remove two vaccinia early transcription termination signals (Yuen and Moss, 1987) contained between position 16 to 40 of MSA1 gene by using the oligonucleotide MAL50 (SEQ ID NO:2).

MAL50: GTGTATTTATAATAAAGAAAAGAAATGAACATAGAAAGAATATGATC

The resulting plasmid was called Mal50+51.

The 510 bp EcoRV/BamHI fragment of Mal50+51 was cloned into the EcoRV/BglII digested SP131Not plasmid. SP131Not was derived from SP131 (Taylor et al., 1991) by modifying the HindIII site to a NotI site. The resulting plasmid was called SP131.5' (FIG. 2).

Modification of the 3' Extremity of the MSA1 Gene. By using the oligonucleotides MAL30 (SEQ ID NO:3) and MAL31 (SEQ ID NO:4), a vaccinia early transcription termination signal was added just after the stop codon and followed by a unique restriction XhoI site. The MAL30 (SEQ ID NO:3) and MAL31 (SEQ ID NO:4) oligonucleotides are complementary as presented below:

Finally, the 957 bp EcoRI fragment from clone 10-1 was ligated into the EcoRI digested SP131HEX. The resulting plasmid was called SP131195. The 5720 AccI/XhoI fragment from SP131195 was cloned into AccI/XhoI digested pIBI24 plasmid. The resulting plasmid was called 24H6195.

EXAMPLE 2

Expression of the Complete MSA1 Gene in the Vaccinia Recombinant vP679 and Immunization Studies in Rabbits Construction of Vaccinia Virus Recombinants. Procedures for transfection of recombinant donor plasmids into tissue culture cells infected with a rescuing vaccinia virus and identification of recombinants by in situ hybridization on nitrocellulose filters were as previously described. (Panicali and Paoletti, 1982; Piccini et al., 1987).

Expression of the Complete MSA1 Gene in vP679. Vero cells were transfected with the plasmid AtiH6195 and infected with the rescuing virus vP410 (Guo et al., 1989).

```
MAL30:    GTTCCTCTAACTTCTTAGGAATATCATTCTTATTAATACTCATGTTAATATTAT
MAL31:ACGTCAAGGAGATTGAAGAATCCTTATAGTAAGAATAATTATGAGTACAATTATAATA
      PstI

ACAGTTTCATTTAATTTTTATC        3'
      TGTCAAAGTAAATTAAAAATAGAGCT    5'
                              XhoI
```

The recombinant virus vP679 was isolated by successive rounds of purification as previously described (Piccini et al., 1987).

Expression Analysis of Vaccinia-expressed MSA1 Proteins. MSA1 immune rabbit serum and monoclonal antibodies have been described (Chang et al., 1989). Immunofluorescence and immunoprecipitation experiments of vaccinia expressed proteins and separation on SDS-containing polyacrylamide gels were conducted as described (Dreyfuss et al., 1984; Guo et al., 1989).

The immunological reagents used in the expression experiments were:

(1) a pool of rabbit sera raised against purified p195 (rabbit K41, K42, and K43) (hereinafter "rabbit serum");

(2) AD9.1 and 5.2—two monoclonal antibodies specific for the C-terminal part of p195 precursor and processed fragments; and (3) CE2.1—monoclonal antibody specific for the N-terminal part of p195 precursor and processed fragment.

The expression of MSA1 in vP679 infected cells was studied by immunofluorescence and immunoprecipitation.

Vero cells were infected at a moi of 0.2 PFU/cell and pulsed with $^{35}$S-methionine. At 48 hours post-infection, cell lysates were harvested and immunoprecipitated with the rabbit serum. Immunoprecipitated proteins were resolved on a 10% Dreyfuss gel and bands visualized by autoradiography.

The MSA1 polypeptide could be detected internally but not on the plasma membrane of vP679-infected cells by immunofluorescence using the rabbit serum or the monoclonal antibodies AD9.1 and 5.2. A weak plasma membrane fluorescence could be detected with monoclonal CE2.1. By immunoprecipitation, a specific protein of an approximate molecular weight of 230 kd is recognized by the rabbit serum and by monoclonal antibodies AD9.1, 5.2, and CE2.1. No consistent submolecular proteins could be detected indicating a lack of processing.

Immunological Evaluation of Rabbit Sera. IFA and ELISA titers were determined by using the procedures described by Siddiqui et al. (1987) and Chang et al. (1989). In vitro parasite growth inhibition was evaluated by using the procedure described by Hui and Siddiqui et al. (1987).

Results of Rabbit Immunization Experiments with vP679. Four rabbits were immunized by intradermal route with $10^8$ pfu of vP679 and boosted twice with the same dose. After the third immunization, one rabbit had an ELISA titer of 6250 and the other three had lower titers. Sera from each of the four rabbits reacted with *Plasmodium falciparum* infected erythrocytes by immunofluorescence analysis. Other routes of injection were tested with similar immunological responses.

The first results obtained with rabbit immunization experiments demonstrated that even if some ELISA titers could be achieved these titers were probably too low to be able to confer protection in the susceptible species. MSA1 is the precursor of several processed proteins covering the surface of merozoites and so the complete MSA1 may not be the more appropriate antigen. In an attempt to mimic the natural situation, fragments of the MSA1 gene have been inserted into various vaccinia recombinants.

EXAMPLE 3

Construction of MSA1/Epstein-Barr Virus gp340 Hybrid Genes

The Epstein-Barr virus gp340 glycoprotein is a plasma membrane anchored protein. gp340 protein possesses at its amino terminus a consensus leader peptide, and at its carboxy terminus a consensus anchor membrane peptide (Whang et al., 1987). These two EBV signal peptides have been used to express fragments of MSA1 on the plasma membrane of recombinant vaccinia infected cells.

The EBV gp340 gene under the control of the vaccinia H6 promoter was obtained: the gp340 5' non-coding sequence (nucleotide −21 to −1) was substituted with the same region of the H6 promoter; at the 3' extremity, after the stop codon, a vaccinia early transcription termination signal sequence was added followed by a SphI site. The resulting plasmid was called 24H6340.

First Construction. The plasmid 24H6340 was digested with EcoRI (position 93 of gp340 coding sequence), treated with Mung-Bean nuclease, digested SphI, and ligated to the 4776 bp PvuII/SphI fragment from 24H6195. The resulting plasmid was called 24-I. The 4994 bp SmaI/XhoI fragment from 24-I was ligated to a SmaI/XhoI COPCS vaccinia donor plasmid (Perkus et al., 1991). The resulting COPCS-I plasmid was obtained and used to isolate the vaccinia recombinant vP718. vP718 infected cells did not express any MSA1 epitopes on the plasma membrane surface as detected by the rabbit serum.

Second Construction. The 6095 bp BalI/SphI fragment from 24-I was ligated with the 163 bp ScaI/SphI fragment from 24H6340. The resulting plasmid was called 24-V. The 163 bp fragment codes for the gp340 anchor membrane domain followed by a stop codon and a vaccinia early transcription termination signal sequence. The 3197 bp SmaI/SphI fragment from 24-V was ligated to a SmaI/SphI COPCS vaccinia donor plasmid (Perkus et al., 1991). The resulting plasmid was called COPCS-V and used to isolate the vaccinia recombinant vP790. vP790 infected cells did not express any MSA1 epitopes on their plasma membrane surface as detected by the rabbit serum and monoclonal antibody CE2.1.

Third Construction. This construction was designed to substitute the gp340 amino leader peptide present in 24-V by the MSA1 leader peptide. The 4693 bp NruI/XbaI fragment from 24-V was ligated with the 1896 bp NruI/XbaI fragment of 24H6195. The resulting plasmid was called 24-XVII. The 3728 bp SmaI/SphI fragment from 24-XVII was ligated to a SmaI/SphI COPCS vaccinia donor plasmid (Perkus et al., 1991). The resulting plasmid was called COPCS-XVII and used to generate the vaccinia recombinant vP843. vP843 infected cells expressed MSA1 epitopes on their plasma membrane surface as detected with monoclonal antibody CE2.1.

EXAMPLE 4

Expression in Vaccinia Recombinants of C-terminal Fragments of MSA1 and Immunization Studies in Rabbits Construction of Vaccinia Donor Plasmids and Isolation of the Corresponding Vaccinia Recombinants. Five vaccinia recombinants expressing various parts the C-terminus of MSA1 were constructed as described below.

First Construction. 24H6195 was digested with HindIII (site at position 99) and BglII (site at position 4676), the extremities were filled in with DNA polymerase I Klenow fragment in presence of dNTPs, and after gel purification, the 3850 bp fragment was ligated intramolecularly. The nucleotidic sequence of the created junction was determined by sequencing:

```
AAA CTA GAA GCT GAT CTT TTT AAA      (SEQ ID NO:5)
Lys Leu Glu Ala Asp Leu Phe Lys      (SEQ ID NO:6)
         34  1559
```

The resulting plasmid was called 24-XII. The 635 bp NruI/SphI fragment from 24-XII was cloned into a COPCS derived vaccinia donor plasmid (Perkus et al., 1991). The resulting plasmid was called COPCS-XII. The recombinant vaccinia virus expressing this construction was called vP788. This recombinant expresses MSA1 epitopes on the plasma membrane of infected cells as detected by the rabbit serum and the monoclonal antibodies AD9.1 and 5.2.

Second Construction. 24H6195 was cut with HindIII (site at position 99) and HpaI (site at position 3702), the HindIII extremity was filled in with DNA polymerase I Klenow fragment in presence of dNTPs, and after gel purification, the 4508 bp fragment was ligated intramolecularly. The nucleotidic sequence of the created junction was determined by sequencing:

```
AAA CTA GAA GCT AAC GAA GCT TTA      (SEQ ID NO:7)
Lys Leu Glu Ala Asn Glu Ala Leu      (SEQ ID NO:8)
         34  1235
```

The resulting plasmid was called 24-XV. The 1708 bp NruII/XhoI fragment from 24-XV was cloned into a COPCS derived vaccinia donor plasmid (Perkus et al., 1991). The resulting plasmid was called COPCS-XV. The recombinant vaccinia virus expressing this construction was called vP806. vP806 infected cells express MSA1 epitopes on their plasma membrane as detected by the monoclonal antibody AD9.1.

Third Construction. The expression results obtained by immunoprecipitation of vP806 infected cell lysate showed the presence of a 72 kd specific protein recognized by the rabbit serum. The theoretical molecular weight of the vP806 partial MSA1 protein is 64 kd. A possible glycosylation could occur at a consensus N-glycosylation site (Asn-Ile-Ser; position 1613 to 1615) and be responsible for the observed increase of molecular weight. The putative role of the glycosylation on the immunogenecity was addressed by modifying the consensus glycosylation sequence. The 505 bp BglII/XhoI fragment of 24H6195 was cloned into a BamHI/XhoI pIBI25 plasmid; the resulting plasmid was called 25Mut. By in vitro mutagenesis, the glycosylation consensus sequence was modified by using the oligonucleotide gly1 (SEQ ID NO:9).

```
                                     (SEQ ID NO:9)
gly1: CAA GAT ATG TTA CAA ATT TCA CAA C
                                     (SEQ ID NO:10)
      Gln Asp Met Leu Gln Ile Ser Gln
                     1613
```

The modification was confirmed by sequencing and the resulting plasmid was called 25Mut1. The 480 bp BstBI/XhoI fragment from 25Mut1 was cloned into the BstBI/XhoI digested plasmid 24-XV. The resulting plasmid was called 24-XV gly1⁻. The 1800 bp SmaI/XhoI fragment from 24-XV gly1⁻ was cloned into the SmaI/XhoI vaccinia donor plasmid COPAK. COPAK plasmid was obtained by substituting the C7L open reading by the K1L open reading frame in the COPCS plasmid (Perkus et al., 1990). The resulting plasmid was called COPAK-XV1⁻. The recombinant vaccinia virus expressing this construction was called vP901.

vP901 infected cells express MSA1 epitopes on their plasma membrane as detected by the rabbit serum and the monoclonal antibody AD9.1. By immunoprecipitation, the specific product of vP901 infected cells recognized by the same reagents has a molecular weight of approximately 68 kd. The molecular weight difference between vP806 and vP901 expressed MSA1 protein can be attributed to the modification of the glycosylation site.

Fourth Construction. The precise localization of the peptide cleavage site in the MSA1 precursor generating the C-terminal gp42 protein is known (ICOPA VII conference, Paris, August 1990, Poster S1.E.11). By protein sequence homology among various *Plasmodium falciparum* strains, this site can be mapped in the Uganda Palo-Alto MSA1 precursor between the amino acids 1332 (Glu) and 1333 (Ala). The DNA fragment coding for the gp42 C-terminal protein was obtained by PCR using the oligonucleotides C001 (SEQ ID NO:11) and C002 (SEQ ID NO:13) and the 24H6195 plasmid as template DNA.

```
C001: GCA ATA TCT GTC ACA ATG           (SEQ ID NO:11)
      Ala Ile Ser Val Thr Met           (SEQ ID NO:12)
      1333                1338

C002: GGCATGCTCGAGATAAAAATTA AAT G       (SEQ ID NO:13)
          SphI XhoI      Stop Ile
```

The PCRed DNA fragment was digested by SphI and cloned into a 24H6195 HindIII filled in with DNA polymerase I Klenow fragment in presence of dNTPs and subsequently SphI digested. The resulting plasmid was called 24-XIX. The nucleotidic sequence of the created junction was determined by sequencing:

```
AAA CTA GAA GCT GCA ATA TCT GTC ACA    (SEQ ID NO: 14)
Lys Leu Glu Ala Ala Ile Ser Val Thr    (SEQ ID NO: 15)
         34  1333
```

The 1200 bp NruI/XhoI fragment of 24-XIX was inserted into the NruI/XhoI vaccinia donor plasmid COPAK H6-1. The resulting plasmid was called COPAK XIX. COPAK H6-1 was obtained by inserting the vaccinia H6 promoter in the COPAK plasmid. The COPAK XIX plasmid was used to generate the vaccinia recombinant vP946. vP946 infected cells expressed MSA1 epitopes on their plasma membrane surface as demonstrated with the monoclonal antibody AD9.1.

Fifth Construction. This construction, COPAK-XXI, is presented in the following Example 5.

Results of Rabbit Immunization Experiments with vP788 and vP806. Two rabbits were immunized by intradermal route with $10^8$ pfu of vP788 or vP806. After three boosts with the same dose, the sera were collected and analyzed by ELISA, IFA, and for the rabbits immunized with vP806, by an in vitro inhibition assay.

Rabbits W127 and W235 were immunized with vP788. Rabbits W292 and W293 were immunized with vP806. ELISA titers of week 11 bleedings are shown in Table I.

TABLE I

| Rabbits | ELISA titers | IFA titers |
|---------|--------------|------------|
| W127    | <50          | 31,250     |
| W235    | <50          | 31,250     |
| W292    | 4,900        | 156,250    |
| W293    | 4,900        | 156,250    |

The results of the in vitro inhibition assay with rabbit sera immunized with vP806 are shown in Table II.

TABLE II

| | % Parasitemia | % Inhibition |
|---|---|---|
| Experiment 1 | | |
| W292 Preimmune | 14.6 | — |
| W292 Week 11 | 11.4 | 22 |
| W293 Preimmune | 15.1 | — |
| W293 Week 11 | 7.3 | 52 |
| Experiment 2 | | |
| W292 Preimmune | 8.5 | — |
| W292 Week 11 | 7.8 | 13 |
| W293 Preimmune | 12.9 | — |
| W293 Week 11 | 6.1 | 54 |

EXAMPLE 5

Expression in Vaccinia Recombinant of N-terminal Fragments of MSA1

First Construction. The MSA1 processed N-terminal fragment is a 83 kd protein. Its N-terminal amino acid is probably the valine residue (position 20) obtained after cleavage of the leader peptide. Its C-terminal amino acid has never been experimentally determined, but by computer analysis (IBI Pustell sequence Analysis Program; IBI, New Haven, Conn.) can be mapped at the amino acid 752 (Gly). By using PCR and specific oligonucleotides, a DNA fragment coding for amino acids 1 to 752 was generated and cloned into the vaccinia donor plasmid COPAK H6-1.

Oligonucleotides C008 (SEQ ID NO:16) and C009 (SEQ ID NO:17) were used to amplify by PCR a 439 bp MSA1 fragment (position 1812 to 2251).

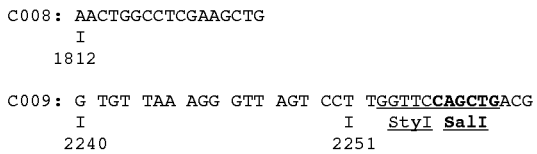

The PCR fragment was digested with XbaI and SalI and ligated at XbaI/SalI pIBI24 derived plasmid. The resulting plasmid was called 24-83. The nucleotidic sequence of the 24-83 inserted fragment was verified. 24-83 was digested with StyI, filled in with DNA polymerase I Klenow fragment in presence of dNTP, digested with XhoI and subsequently ligated with the XhoI digested PCR fragment generated with oligonucleotides C001 (SEQ ID NO:11) and C002 (SEQ ID NO:13). The resulting plasmid was called 24-(83+42). The nucleotidic sequence flanking the restored StyI site was determined:

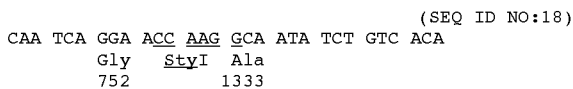

The 1590 bp XbaI/SphI fragment of 24-(83+42) was inserted into the 4696 bp XbaI/SphI fragment of 24-XVII plasmid. The resulting plasmid was called 24-XXI. The 3480 bp NruI/XhoI fragment of 24-XXI was inserted into the NruI/XhoI vaccinia donor plasmid COPAK H6-1. The resulting plasmid was called COPAK-XXI.

REFERENCES

1. Chang, S. P., Hui, G. S. N., Kato, A., Siddiqui, W. A., Proc. Natl. Acad. Sci. USA 86, 6343–6347 (1989).
2. Chang, S. P., Kramer, K. J., Yamaga, K. M., Kato, A., Case, S. E., Siddiqui, W. A., Exp. Para. 67, 1–11 (1988).
3. Cheung, A., Leban, J., Shaw, A. R., Merkli, B., Stocker, J., Chizzolini, C., Sander, C., Perrin, L. H., Proc. Natl. Acad. Sci. USA. 83, 8328–8332 (1986).
4. Clewell, D. B., J. Bacteriol. 110, 667–676 (1972).
5. Clewell, D. B. and Helinski, D. R., Proc. Natl. Acad. Sci. USA 62, 1159–1166 (1969).
6. Dreyfuss, G., Adam, S. A., Choi, Y. D., Mol. Cell. Biol. 4, 415–423 (1984).
7. Guo, P., Goebel, S., Davis, S., Perkus, M. E., Languet, B., Desmettre, P., Allen, G., Paoletti, E., J. Virol. 63, 4189–4198 (1989).
8. Hall, R., Hyde, J. E., Goman, M., Simmons, D. L., Hope, I. A., Mackay, J., Richle, R., Nature 311, 279–392 (1984).
9. Herrera, S., Herrera, M. A., Perlaza, B. L., Burki, Y., Caspers, P., Dobeli, H., Rotmann, D., Certa, U., Proc. Natl. Acad. Sci. USA 87, 4017–4021 (1990).
10. Holder, A. A., Prog. Allergy 41, 72–97 (1988a).
11. Holder, A. A., Freeman, R. R., Nicholls, S. C., Parasit. Immunol. 10, 607–617 (1988b).
12. Hui, G. S. N., Siddiqui, W. A., Exp. Para. 64, 519–522 (1987).
13. Knapp, B., Shaw, A., Hundt, E., Enders, B., Kupper, H. A., Behring Inst. Mitt. 82, 349–359 (1988).
14. Kunkel, T. A., Roberts, J. D., Zakour, R. A., Methods Enzymol. 154, 367–382 (1987).
15. Lyon, J. A., Haynes, J. D., Diggs, C. L., Chulay, J. D., Haidaris, C. G., Pratt-Rossiter, J., J. Immunol. 138, 895–901 (1987).
16. Maniatis, T., Fritsch, E. F., Sambrock, J., In Molecular Cloning: A Laboratory Manual (Cold Spring Harbor Laboratory, Cold Spring Harbor, N.Y.) (1982).
17. Panicali, D., Paoletti, E., Proc. Natl. Acad. Sci. USA 79, 4927–4931 (1982).
18. Patarroyo, M. E., Amador, R., Clavijo, P., Moreno, A., Guzman, F., Romero, P., Tascon, R., Franco, A., Murillo, L. A., Ponton, G., Trujillo, G., Nature 332, 158–161 (1988).
19. Patarroyo, M. E., Romero, P., Torres, M. L., Clavijo, P., Moreno, A., Martinez, A., Rodriguez, R., Guzman, F., Cabezas, E., Nature 328, 629–632 (1987).
20. Perkus, M. E., Goebel, S. J., Davis, S. W., Johnson, G. P., Limbach, K., Norton, E. K., Paoletti, E., Virology 179, 276–286 (1990).
21. Perkus, M., Goebel, S., Davis, S., Johnson, G., Norton, E., and Paoletti, E., Virol. 180, 406–410 (1991).
22. Perrin, L. H., Merkli, B., Loche, M., Chizzolini, C., Smart, J., and Richle, R., J. Exp. Med. 160, 441–451 (1984).
23. Peterson, M. G., Coppel, R. L., Moloney, M. B., Kemp, D. J., Mol. Cell. Biol. 8, 2664–2667 (1988).
24. Piccini, A., Perkus, M. E. and Paoletti, E., In Methods in Enzymology, Vol. 153, eds. Wu, R., and Grossman, L., (Academic Press) pp. 545–563 (1987).
25. Sambrook, J., Fritsch, E. F., and Maniatis, T., In Molecular cloning: A laboratory manual, 2nd edition, (Cold Spring Harbor Press, NY) (1989).
26. Sanger, F., Nicklen, S., Coulson, A. R., Proc. Natl. Acad. Sci. USA 74, 5463–5467 (1977).
27. Siddiqui, W. A., Tam, L. Q., Kan, S. C., Kramer, K. J., Case, S. E., Palmer, K. L., Yamaga, K. M., Hui, G. S., Infect. Immun. 52, 314–318 (1986).
28. Siddiqui, W. A., Tam, L. Q., Kramer, K. J., Hui, G. S. N., Case, S. E., Yamaga, K. M., Chang, S. P., Chan, E. B. T., Kan, S. C., Proc. Natl. Acad. Sci. USA 84, 3014–3018 (1987).
29. Tanabe, K., Mackay, N., Goman, M., Scaife, J. G., J. Mol. Biol. 195, 273–287 (1987).
30. Taylor, J., Weinberg, R., Kawaoka, L., Webster, R. G., and Paoletti, E., Vaccine 6, 504–506 (1988a).
31. Taylor, J., Weinberg, R., Languet, B., Desmettre, P., and Paoletti, E., Vaccine 6, 497–503 (1988b).
32. Taylor, J., Pincus, S., Tartaglia, J., Richardson, C., Alkhatib, G., Briedis, D., Appel, M., Norton, E., and Paoletti, E., J. Virol. 65, in press (1991).
33. Whang, Y., Silberklang, M., Morgan, A., Munshi, S., Lenny, A. B., Ellis, R. W., Kieff, E., J. Virol. 61, 1796–1807 (1987).
34. Yuen, L., Moss, B., Proc. Natl. Acad. Sci. USA 84, 6417–6421 (1987).

What is claimed is:

1. A recombinant vaccinia virus or avipox virus containing therein DNA coding for *Plasmodium falciparum* Merozoite Surface Antigen 1 or for a subfragment or *Plasmodium falciparum* Merozoite Surface Antigen 1, said DNA operably linked to a promoter for controlling expression of the DNA, wherein said subfragment of *Plasmodium falciparum* Merozoite Surface Antigen 1 consists of an N-terminal 83 kD fragment or the N-terminal 83 kD fragment plus a C-terminal gp42 fragment of *Plasmodium falciparum* Merozoite Surface Antigen 1.

2. The recombinant vaccinia virus or avipox virus of claim 1 which is an avipox virus.

3. The recombinant vaccinia virus or avipox virus of claim 2 wherein the avipox virus is a canarypox virus.

4. The recombinant vaccinia virus or avipox virus of claim 1 containing therein DNA coding for Plasmodium Merozoite Surface Antigen 1 of the Uganda Palo-Alto isolate of *Plasmodium falciparum* operably linked to a promoter for controlling expression of the DNA.

5. A recombinant vaccinia virus or avipox virus containing therein DNA coding for a subfragment of Plasmodium Merozoite Surface Antigen 1 of the Uganda Palo-Alto isolate of *Plasmodium falciparum* operably linked to a promoter for controlling expression of the DNA, wherein said subfragment of Plasmodium Merozoite Surface Antigen 1 consists of amino acids 1–752 or amino acids 1–752 and 1333–1726 of Plasmodium Merozoite Surface Antigen 1.

6. An immunological composition for inducing an immunological response in a host animal inoculated with said composition, said composition comprising a carrier in admixture with a recombinant vaccinia virus or avipox virus as claimed in any one of claims 1–5.

7. A method for producing a Plasmodium Merozoite Surface Antigen 1 or subfragment thereof which comprises infecting a host cell in vitro with a recombinant vaccinia virus or avipox virus as claimed in any one of claims 1–5.

8. A method for inducing an immunological response in a host comprising administering a recombinant vaccinia virus or avipox virus as claimed in any one of claims 1–5.

\* \* \* \* \*

UNITED STATES PATENT AND TRADEMARK OFFICE
CERTIFICATE OF CORRECTION

PATENT NO. : 6,214,353 B1
DATED : April 10, 2001
INVENTOR(S) : Enzo Paoletti et al.

It is certified that error appears in the above-identified patent and that said Letters Patent is hereby corrected as shown below:

Title page,
Item [75], Inventors: Change "Charles de Taisne, Lyons (FR)" to -- Charles de Taisne, Albany, NY (US) --
Item [75], Inventors: Change "Wasim A. Siddigui" to -- Wasim A. Siddiqui --

Signed and Sealed this

Sixteenth Day of October, 2001

*Attest:*

NICHOLAS P. GODICI
*Attesting Officer*     *Acting Director of the United States Patent and Trademark Office*

SEQUENCE LISTING

<160> NUMBER OF SEQ ID NOS: 18

<210> SEQ ID NO 1
<211> LENGTH: 58
<212> TYPE: DNA
<213> ORGANISM: Vaccinia virus

<400> SEQUENCE: 1
aaagaatatg atcttcatta cgatacaaac ttaacggata tccctatagt gagtcgta        58

<210> SEQ ID NO 2
<211> LENGTH: 47
<212> TYPE: DNA
<213> ORGANISM: Vaccinia virus

<400> SEQUENCE: 2
gtgtatttat aataaagaaa agaaatgaac atagaaagaa tatgatc        47

<210> SEQ ID NO 3
<211> LENGTH: 76
<212> TYPE: DNA
<213> ORGANISM: Vaccinia virus

<400> SEQUENCE: 3
gttcctctaa cttcttagga atatcattct tattaatact catgttaata ttatacagtt        60
tcatttaatt tttatc        76

<210> SEQ ID NO 4
<211> LENGTH: 84
<212> TYPE: DNA
<213> ORGANISM: Vaccinia virus

<400> SEQUENCE: 4
acgtcaagga gattgaagaa tccttatagt aagaataatt atgagtacaa ttataatatg        60
tcaaagtaaa ttaaaaatag agct        84

<210> SEQ ID NO 5
<211> LENGTH: 24
<212> TYPE: DNA
<213> ORGANISM: Vaccinia virus

<400> SEQUENCE: 5
aaactagaag ctgatctttt taaa        24

<210> SEQ ID NO 6
<211> LENGTH: 8
<212> TYPE: PRT
<213> ORGANISM: Vaccinia virus

<400> SEQUENCE: 6

Lys Leu Glu Ala Asp Leu Phe Lys
 1               5

-continued

<210> SEQ ID NO 7
<211> LENGTH: 24
<212> TYPE: DNA
<213> ORGANISM: Vaccinia virus

<400> SEQUENCE: 7
aaactagaag ctaacgaagc ttta                                          24

<210> SEQ ID NO 8
<211> LENGTH: 8
<212> TYPE: PRT
<213> ORGANISM: Vaccinia virus

<400> SEQUENCE: 8

Lys Leu Glu Ala Asn Glu Ala Leu
 1               5

<210> SEQ ID NO 9
<211> LENGTH: 25
<212> TYPE: DNA
<213> ORGANISM: Vaccinia virus

<400> SEQUENCE: 9
caagatatgt tacaaatttc acaac                                         25

<210> SEQ ID NO 10
<211> LENGTH: 8
<212> TYPE: PRT
<213> ORGANISM: Vaccinia virus

<400> SEQUENCE: 10

Gln Asp Met Leu Gln Ile Ser Gln
 1               5

<210> SEQ ID NO 11
<211> LENGTH: 18
<212> TYPE: DNA
<213> ORGANISM: Vaccinia virus

<400> SEQUENCE: 11
gcaatatctg tcacaatg                                                 18

<210> SEQ ID NO 12
<211> LENGTH: 6
<212> TYPE: PRT
<213> ORGANISM: Vaccinia virus

<400> SEQUENCE: 12

Ala Ile Ser Val Thr Met
 1               5

<210> SEQ ID NO 13
<211> LENGTH: 26
<212> TYPE: DNA
<213> ORGANISM: Vaccinia virus

<400> SEQUENCE: 13
ggcatgctcg agataaaaat taaatg                                        26

<210> SEQ ID NO 14
<211> LENGTH: 27
<212> TYPE: DNA
<213> ORGANISM: Vaccinia virus

```
<400> SEQUENCE: 14
aaactagaag ctgcaatatc tgtcaca                                          27

<210> SEQ ID NO 15
<211> LENGTH: 9
<212> TYPE: PRT
<213> ORGANISM: Vaccinia virus

<400> SEQUENCE: 15

Lys Leu Glu Ala Ala Ile Ser Val Thr
 1               5

<210> SEQ ID NO 16
<211> LENGTH: 17
<212> TYPE: DNA
<213> ORGANISM: Vaccinia virus

<400> SEQUENCE: 16
aactggcctc gaagctg                                                     17

<210> SEQ ID NO 17
<211> LENGTH: 34
<212> TYPE: DNA
<213> ORGANISM: Vaccinia virus

<400> SEQUENCE: 17
gtgttaaagg gttagtcctt ggttccagct gacg                                  34

<210> SEQ ID NO 18
<211> LENGTH: 30
<212> TYPE: DNA
<213> ORGANISM: Vaccinia virus

<400> SEQUENCE: 18
caatcaggaa ccaaggcaat atctgtcaca                                       30
```